(12) United States Patent
Nagane et al.

(10) Patent No.: US 10,239,865 B2
(45) Date of Patent: Mar. 26, 2019

(54) BISPHENOLS CONTAINING PENDANT CLICKABLE MALEIMIDE GROUP AND POLYMERS THEREFROM

(71) Applicant: Council of Scientific & Industrial Research, New Delhi (IN)

(72) Inventors: Samadhan Suresh Nagane, Maharashtra (IN); Sachin Suresh Kuhire, Maharashtra (IN); Prakash Purushottam Wadgaonkar, Maharashtra (IN)

(73) Assignee: Council of Scientific & Industrial Research (IN)

(*) Notice: Subject to any disclaimer, the term of this patent is extended or adjusted under 35 U.S.C. 154(b) by 0 days.

(21) Appl. No.: 15/544,183

(22) PCT Filed: Jan. 15, 2016

(86) PCT No.: PCT/IN2016/050015
§ 371 (c)(1),
(2) Date: Jul. 17, 2017

(87) PCT Pub. No.: WO2016/113760
PCT Pub. Date: Jul. 21, 2016

(65) Prior Publication Data
US 2018/0009788 A1    Jan. 11, 2018

(30) Foreign Application Priority Data
Jan. 15, 2015 (IN) .............................. 129/DEL/2015

(51) Int. Cl.
| | | |
|---|---|---|
| C08G 63/81 | (2006.01) |
| C08G 64/12 | (2006.01) |
| C07D 209/48 | (2006.01) |
| C07D 403/06 | (2006.01) |
| C08G 63/685 | (2006.01) |
| C08G 63/688 | (2006.01) |

(52) U.S. Cl.
CPC ......... *C07D 403/06* (2013.01); *C07D 209/48* (2013.01); *C08G 63/685* (2013.01); *C08G 63/6886* (2013.01); *C08G 63/81* (2013.01); *C08G 64/12* (2013.01)

(58) Field of Classification Search
CPC ................ C07D 209/00; C07D 209/48; C07D 207/448; C07C 39/23; C08G 63/685
See application file for complete search history.

(56) References Cited

U.S. PATENT DOCUMENTS

| | | | | |
|---|---|---|---|---|
| 3,862,232 A | * | 1/1975 | Lednicer ................ | C07C 45/46 250/396 R |
| 5,344,910 A | * | 9/1994 | Sybert .................... | C08G 64/12 528/125 |
| 2005/0222334 A1 | * | 10/2005 | Srinivasan .......... | C07D 209/34 525/178 |
| 2005/0288517 A1 | * | 12/2005 | Rai ...................... | C07D 209/46 548/472 |
| 2007/0123687 A1 | * | 5/2007 | Balakrishnan ........ | C08G 63/64 528/196 |
| 2007/0123713 A1 | * | 5/2007 | Raj ..................... | C07D 209/48 548/476 |
| 2007/0135612 A1 | * | 6/2007 | Ganesan .............. | C07D 209/46 528/196 |
| 2008/0242873 A1 | * | 10/2008 | Basale ................ | C07D 209/46 548/472 |
| 2010/0081831 A1 | * | 4/2010 | Bhotla ................ | C07D 307/83 549/308 |
| 2011/0151262 A1 | * | 6/2011 | Heuer ................. | C07D 209/46 428/412 |
| 2016/0060403 A1 | * | 3/2016 | Mahood .................. | C08J 5/18 428/220 |
| 2016/0340307 A1 | * | 11/2016 | Bhotla .................. | C08G 64/12 |

FOREIGN PATENT DOCUMENTS

| | | | |
|---|---|---|---|
| CN | 103373950 A | * | 10/2013 |
| EP | 0617070 A2 | | 9/1994 |
| EP | 1582549 A1 | | 10/2005 |
| EP | 2338880 A2 | | 6/2011 |
| WO | WO-2015/107467 A1 | | 7/2015 |

* cited by examiner

Primary Examiner — Liam J Heincer
(74) Attorney, Agent, or Firm — Blank Rome LLP

(57) ABSTRACT

The patent discloses bisphenol monomers of formula I with pendant maleimide group connected via alkylene spacer and preparation thereof. Also, it discloses polymers based on bisphenol monomers containing pendant clickable maleimide group. Further, it provides a process for the preparation of polymers possessing pendant clickable maleimide groups based on bisphenols containing pendant maleimide group. Formula (I) wherein, x is an integer selected from 0 to 10.

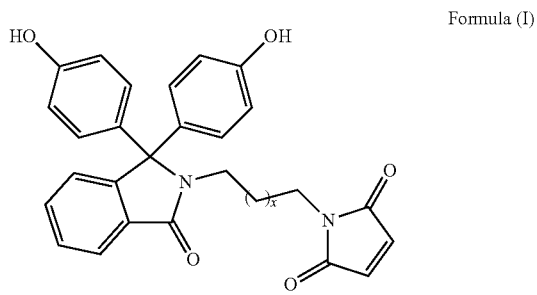

Formula (I)

5 Claims, 4 Drawing Sheets

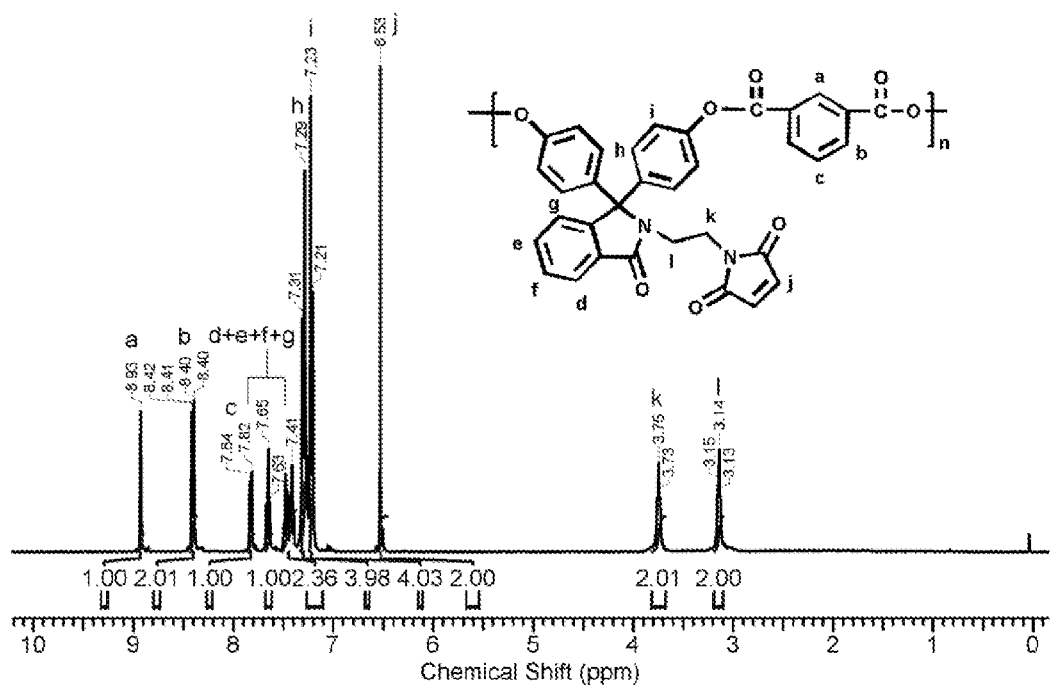
Fig: 2

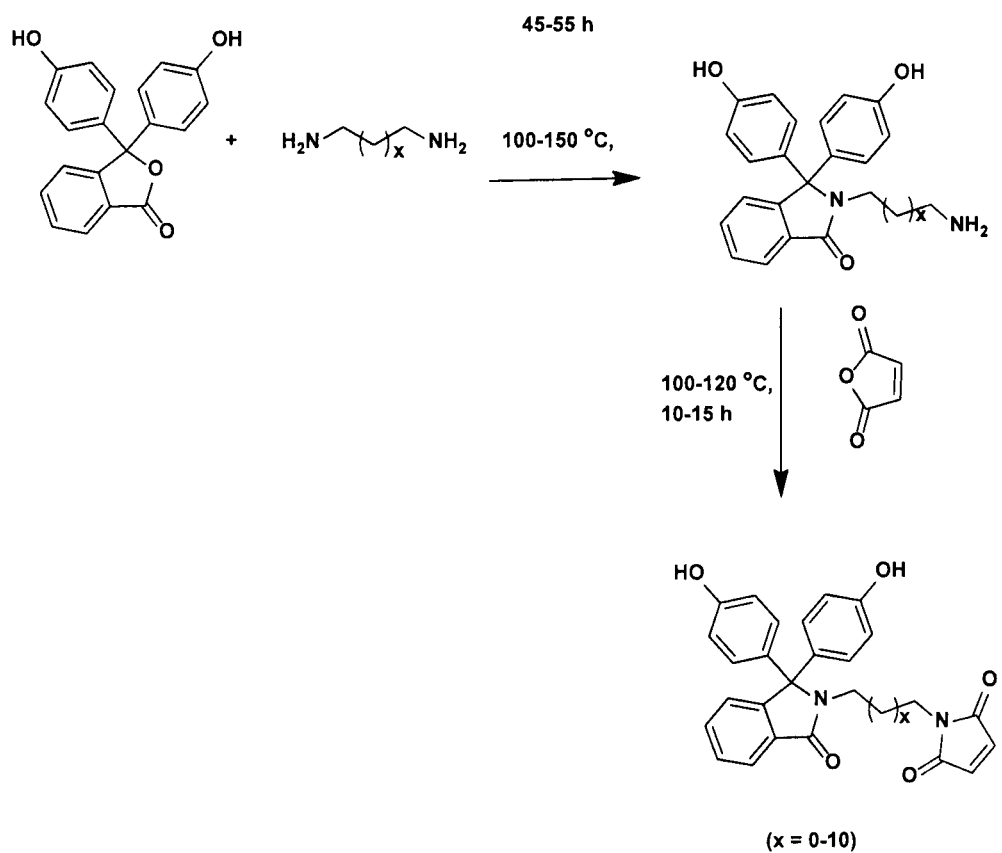
Fig: 3

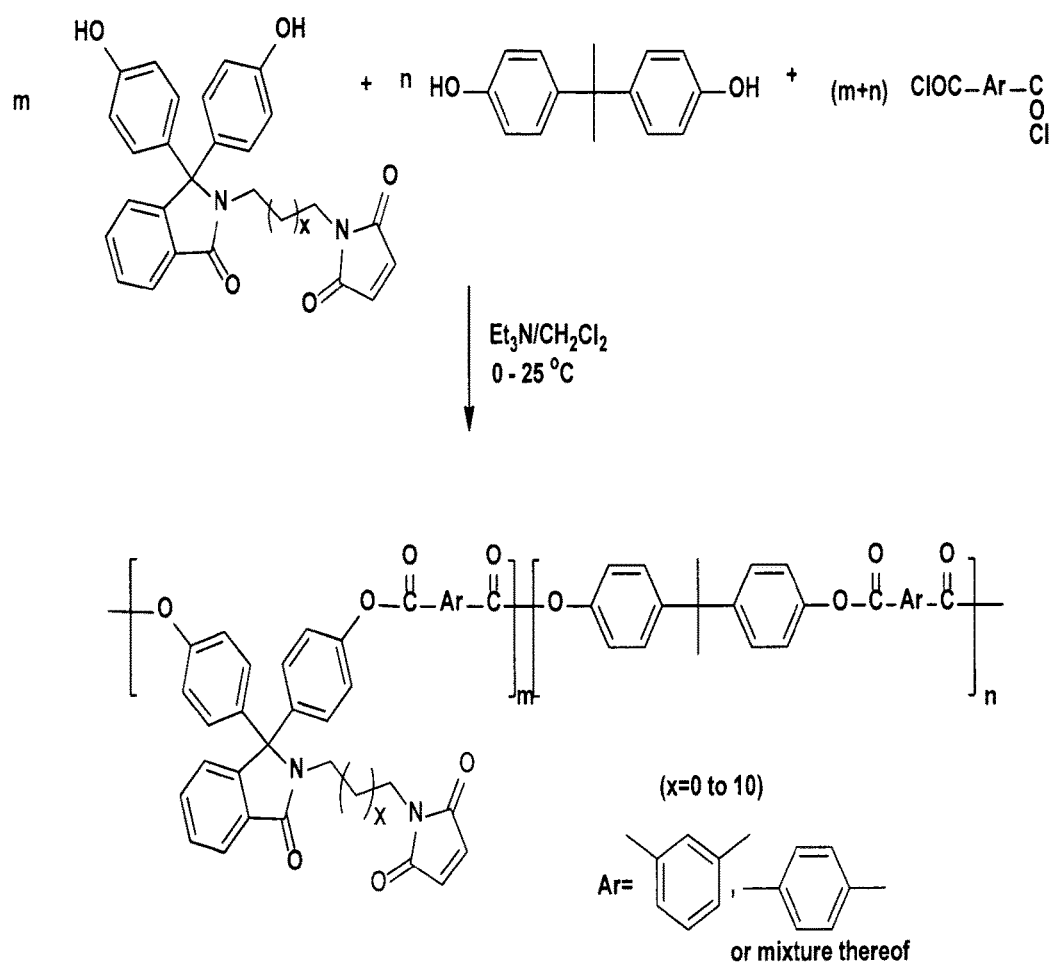
Fig: 4

BISPHENOLS CONTAINING PENDANT CLICKABLE MALEIMIDE GROUP AND POLYMERS THEREFROM

RELATED APPLICATIONS

This application is a national phase of PCT/IN2016/050015, filed on Jan. 15, 2016, which claims the benefit of Indian Application No. 129/DEL/2015, filed on Jan. 15, 2015. The entire contents of these applications are incorporated herein by reference.

FIELD OF THE INVENTION

The present invention relates to bisphenol monomers containing pendant clickable maleimide group. Particularly, present invention relates to a simple and cost efficient process for the preparation of bisphenol monomers containing pendant clickable maleimide group. More particularly, the present invention relates to bisphenol monomers containing pendant clickable maleimide group and use of these bisphenol monomers for the preparation of polymers.

BACKGROUND AND PRIOR ART OF THE INVENTION

Polymers containing maleimide group(s) either at the chain end(s) or as pendant groups are of great interest in view of the demonstrated capability of maleimide group to participate in highly efficient chemical reactions such as addition of thiol over the vinyl double bond and Diels-Alder reaction with suitable dienes such as furans and anthryl. Polymers possessing maleimide group(s) at chain end(s) are accessible by chain polymerization of addition monomers with appropriate (protected) maleimide containing initiator or by chemical modification of functionally-terminated polymers with maleimide containing reagents. Polymers bearing pendant maleimide groups have been synthesized by chain polymerization of addition monomers or by step growth polymerization of condensation monomers containing maleimide groups. Chemical modification approach has also been employed to synthesize polymers with pendant maleimide groups.

Bisphenols are a versatile class of monomers and are useful as building blocks for synthesis of a range of polymers such as polycarbonates, polyesters, polyether sulfones, polyether ketones, epoxies, etc. Furthermore, bisphenols possessing pendant functional groups provide an access to above mentioned polymers containing the respective pendant functional groups which could be subsequently exploited as reactive sites for chemical modifications. Bisphenols containing pendant functional groups such as hydroxyl, halogen, carboxyl, primary amine, tertiary amine, azido, furyl, alkene, etc are known in the literature. However, examples of bisphenols containing pendant maleimide group are limited. Bisphenols containing pendant maleimide groups find applications in the preparation of high performance polymers such as polycarbonates, polyesters, polyether sulfones, polyetherketones, epoxies, etc. The pendant maleimide groups provide interesting opportunities for chemical modifications and crosslinking reactions.

U.S. Pat. No. 7,135,577 B2 and US 2005/0222334 A1 discloses a method for producing and purifying 2-hydrocarbyl-3,3bis(4-hydroxyaryl)phthalimidine monomers, and polycarbonates as well as other polymers derived utilizing the monomers. The method comprises forming a reaction mixture comprising at least one substituted or unsubstituted phenolphthalein, at least one substituted or unsubstituted primary hydrocarbyl amine, and an acid catalyst; and heating the reaction mixture to a temperature of less than 180° C. to remove a distillate comprising water and form a crude 2-hydrocarbyl-3,3-bis(4-hydroxyaryl)phthalimidine product; where the 2-hydrocarbyl-3,3-bis(4-hydroxyaryl)phthalimidine has a formula:

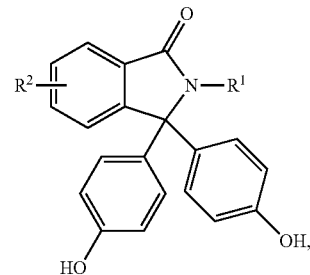

where $R^1$ is selected from the group consisting of a hydrogen and a hydrocarbyl group, and $R^2$ is selected from the group consisting of a hydrogen, a hydrocarbyl group, and a halogen.

CN103373950A discloses a maleimide group-containing bisphenol monomer, it's synthetic method and applications. The maleimide containing bisphenol monomers, of the following structure:

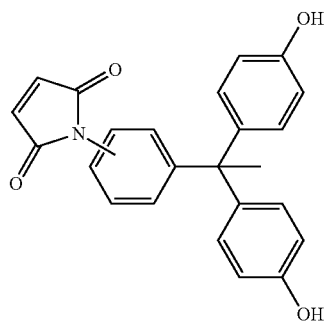

Wherein, the maleimide groups are directly attached to aromatic ring have been disclosed.

U.S. Pat. No. 4,514,334 relates a polyphenolic compound of the formula, wherein Ar is a mono, -di- or trinuclear aromatic $C_{6-14}$ hydrocarbon radical; R is hydrogen or a $C_1$-$C_5$ alkyl radical; each X substituent is independently selected from H, Cl, Br, $C_1$-$C_5$ alkyl and phenyl; and n is either 2, 3 or 4.

U.S. Pat. No. 7,425,603 B2, US 2007/0123682 A1 and US20070123713 A relates to a process of forming a polycyclic dihydroxy compound as shown below.

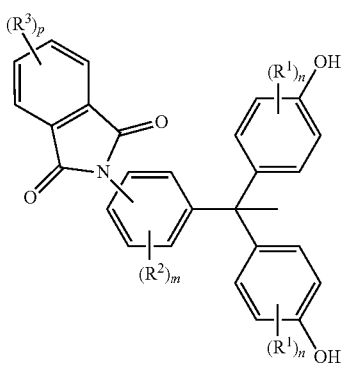

wherein $R^1$, $R^2$ and $R^3$ are independently at each occurrence selected from the group consisting of a cyano functionality, a halogen, an aliphatic functionality having 1 to 10 carbons, a cycloaliphatic functionality having 3 to 10 carbons, and an aromatic functionality having 6 to 10 carbons; and wherein each occurrence of "n", "m", and "p" independently has a value of 0, 1, 2, 3, or 4. Also described are polycyclic dihydroxy compounds of Formula (I) in which the phthalimide group is meta to the triaryl-substituted carbon.

Article titled, "Maleimide-containing polyamides" by Camelia Hulubei in Materiale Plastice 45Nr. 3, 228, 2008 reports functional polyamides with pendant hydroxyl groups prepared by the direct polycondensation of 5,5'-methylene-bissalicylic acid, with various diamines (p-phenylenediamine, 4,4'-oxydianiline and 4,4'-methylenedianiline) in N-methyl-2-pyrrolidone, using triphenyl phosphite and pyridine as condensing agents. The resulting polymers were chemically modified with 4-maleimidobenzoyl chloride, resulting in polyamides with maleimide pendant groups. The polymers were soluble in dipolar aprotic solvents such as dimethylsulfoxide, dimethylformamide, and were thermally stable up to 314° C. The chemically modified polyamides exhibited better solubility and thermal stability than their unmodified counterparts.

Article titled, "Synthesis and post-polymerization modification of maleimide-containing polymers by 'thiol-ene' click and Diels-Alder chemistries" by Daniel J. Hall et. al in Polym. Int., Volume 60, Issue 8, pages 1149-1157, August 2011 reviews the versatility and utility of the maleimide group in the efficient functionalization of polymers by both 'thiol-ene' Michael addition and Diels-Alder cycloaddition chemistries. US 2005/0228137 A1 relates to a polymer blend consisting essentially of at least one thermoplastic polymer, and a polymer comprising structural units derived from a 2-hydrocarbyl-3,3-bis(4-hydroxyaryl)phthalimidine.

Article titled, "Phenolphthalein-based cardo poly(arylene ether sulfone): Preparation and application to separation membranes." Gao, N. and Zhang, S. in J. Appl. Polym. Sci., 128: 1-12. doi:10.1002/app.38810 reviews the synthesis of phenolphthalein-based cardo poly(arylene ether sulfone)s, including synthesis of cardo bisphenols and their polymers, and their application to gas separation membranes.

U.S. Pat. No. 4,134,936 discloses novel copolycarbonates exhibiting generally improved impact resistance, clarity and flame resistance are prepared by blending a polycarbonate of a trityldiol such as phenolphthalein and a polycarbonate of another diol such as bisphenol-A under conditions of temperature and/or shear sufficient to cause reaction of the polycarbonates.

However, bisphenols possessing pendant maleimide groups which are connected via alkylene spacer are not reported in the prior art. Therefore, it is the need to develop bisphenols starting from commercially available and inexpensive chemicals and possessing pendant maleimide group which is connected via alkylene spacer.

OBJECTIVE OF THE INVENTION

The main objective of the present invention is to provide bisphenol monomers with pendant maleimide groups connected via alkylene spacer.

Another objective of the present invention is to provide a simple and cost efficient process for the preparation of bisphenol monomers containing pendant maleimide group starting from commercially available and inexpensive chemicals.

Yet another objective of present invention is to provide polymers having pendant clickable maleimide groups based on bisphenol monomers.

Still another objective of present invention is to provide a process for the preparation of polymers having pendant clickable maleimide groups based on bisphenol monomers.

SUMMARY OF THE INVENTION

Accordingly, present invention provides a compound of formula (I)

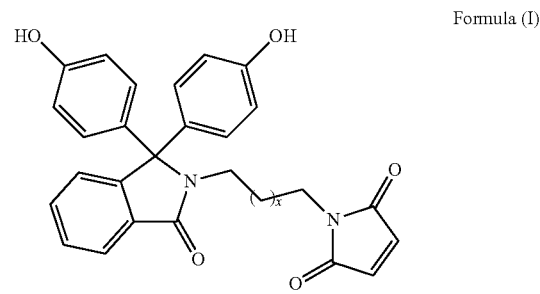

Formula (I)

wherein, x is an integer selected from 0 to 10.

In an embodiment, present invention provides a process for the synthesis of compound of formula I comprising the steps of:
a. stirring the reaction mixture comprising alkylenediamine and phenolphthalein in the molar ratio ranging between 10:1 to 20:1 for period in the range of 45 to 55 h at temperature in the range of 100 to 150° C. to afford phenolphthalein N-(aminoalkyl)lactam; and
b. stirring the reaction mixture comprising phenolphthalein N-(aminoalkyl)lactam as obtained in step (a), maleic anhydride and glacial acetic acid for period in the range of 10 to 15 h at temperature in the range of 100 to 120° C. to afford compound of formula I.

In another embodiment of the present invention, said compound is useful for the preparation of polymers selected from polyesters, polycarbonates, polyether sulfones, polyetherketones, epoxy resins, and the like but not limited to polyesters of formula II

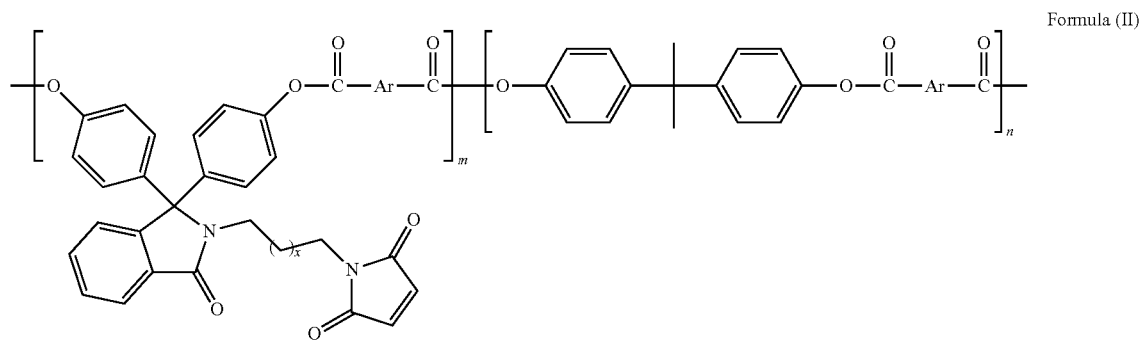

Formula (II)

wherein; x is selected from 0 to 10 and Ar is selected from

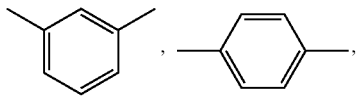

or mixture thereof.

In an embodiment, present invention provides a process for the synthesis of polyesters of formula II comprising the steps of:
 a) adding a solution of isophthaloyl chloride in dichloromethane to a phenolphthalein N-(maleimidoalkyl) lactam in dichloromethane in the presence of triethylamine and maintaining the reaction temperature at 0 to 10° C.; and
 b) stirring the reaction mixture of step (a) for period in the range of 20 to 30 min to get desired aromatic polyester.

BRIEF DESCRIPTION OF THE DRAWINGS

FIG. 2 represents $^1$H-NMR spectrum (in CDCl$_3$) of polyester obtained by polycondensation of phenolphthalein N-(3-maleimidoethyl)lactam and isophthaloyl chloride.

FIG. 3 represents a process for the preparation of bisphenol monomers containing pendant maleimide groups.

FIG. 4 represents a process for the preparation of polyesters based on bisphenols with pendant maleimide group.

DETAILED DESCRIPTION OF THE INVENTION

Figure 1:
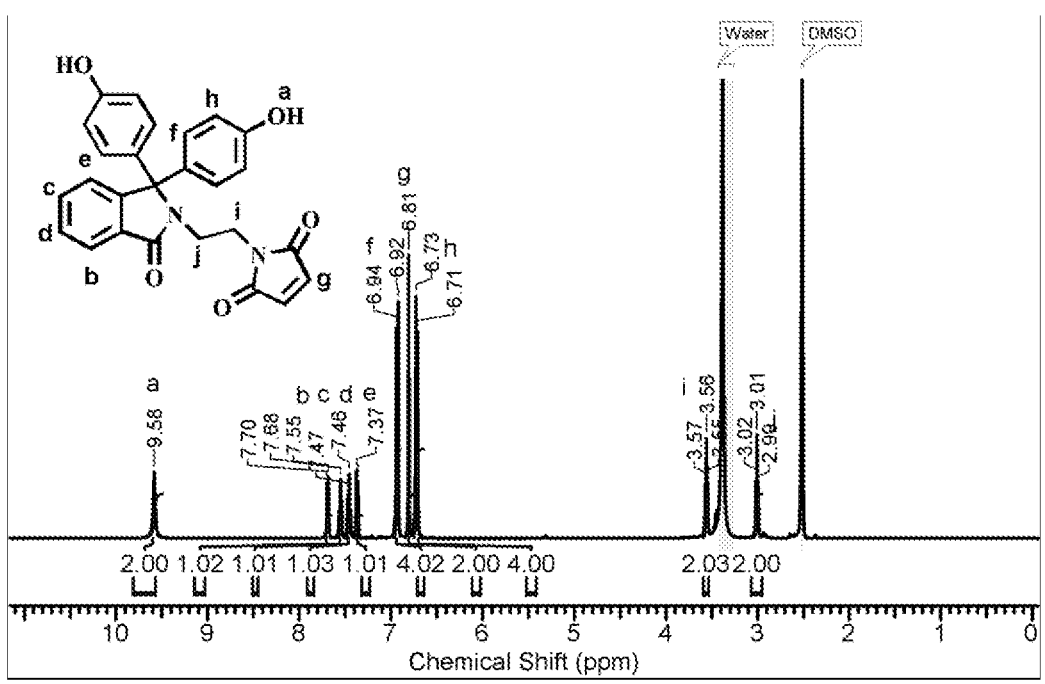
FIG. 1 represents $^1$H-NMR spectrum (in DMSO $d_6$) of phenolphthalein N-(3-maleimidoethyl)lactam.

Present invention provides bisphenol monomers of formula (I) containing pendant maleimide group which is connected via alkylene spacer.

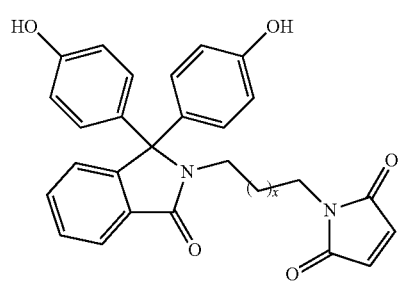

Formula (I)

wherein, x is an integer selected from 0 to 10.

In another aspect, compound of formula (I) is phenolphthalein N-(maleimidoethyl)lactam.

The present invention provides a simple and cost efficient process for the preparation of bisphenol monomer containing pendant maleimide group using phenolphthalein as a commercially available starting material employing simple organic transformations. In another aspect, the present invention provides polymers based on bisphenol monomers containing pendant clickable maleimide group.

The present invention provides a process for the preparation of bisphenol monomers containing pendant maleimide groups and the said process comprising the steps of:

a) stirring the reaction mixture comprising alkylenediamine and phenolphthalein in the molar ratio ranging between 10:1 to 20:1 for period in the range of 45 to 55 h at temperature in the range of 100 to 150° C. to afford phenolphthalein N-(aminoalkyl)lactam; and b) stirring the reaction mixture comprising phenolphthalein N-(aminoalkyl)lactam as obtained in step (a), maleic anhydride and glacial acetic acid for period in the range of 10 to 15 h at temperature in the range of 100 to 120° C. to afford compound of formula I.

The process for the preparation of bisphenol monomers containing pendant maleimide groups as described above is shown in FIG. 3.

The present invention provides compounds of formula (I) with thermally cross linkable maleimide group for synthesis of polymers selected from, but not limited to polyesters, polycarbonates, polyether sulfones, polyetherketones, epoxy resins, and the like.

The present invention provides polyester of formula (II) based on bisphenol monomer with pendant maleimide group of formula (I).

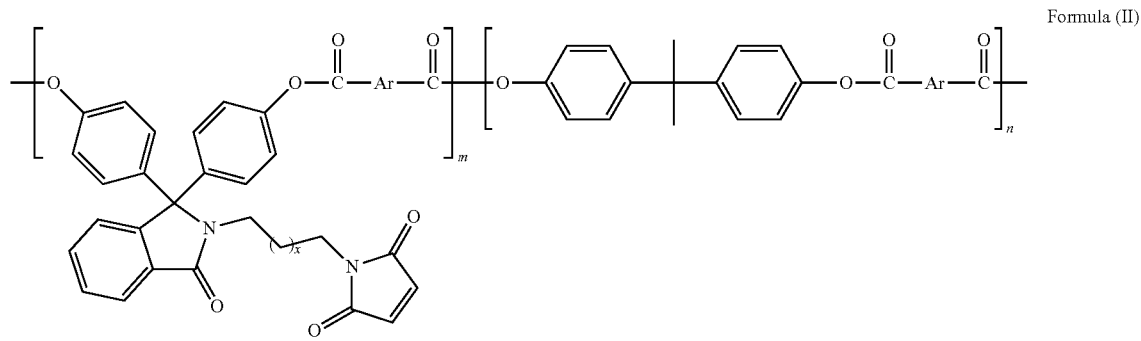

wherein, x is selected from 0 to 10 and Ar is selected from the following:

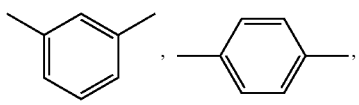

or mixture thereof.

The present invention provides a process for the preparation of polyesters starting from bisphenols with pendant maleimide group as disclosed herein comprising the steps of:
  a) adding a solution of isophthaloyl chloride in dichloromethane to a solution phenolphthalein N-(maleimidoalkyl)lactam in dichloromethane in the presence of triethylamine and maintaining the reaction temperature at 0° C.; and
  b) stirring the reaction mixture of step (a) for 30 min at 0° C. and for 1 h at 25° C. to get desired aromatic polyester.

The process for the preparation of polyesters based on bisphenols with pendant maleimide group is shown in FIG. 4.

In a preferred aspect, these polymers of present invention containing pendant maleimide groups are capable of undergoing thiol-ene reaction and Diels-Alder reaction to form graft copolymers.

In another preferred aspect, these polymers of present invention containing pendant maleimide groups can be crosslinked thermally or by using bis-furan reagents into thermosetting resins.

EXAMPLES

The following examples are given by way of illustration and therefore should not be construed to limit the scope of the invention.

Example: 1

A) Synthesis of Phenolphthalein N-(3-aminoethyl)lactam

Into a 500 mL three-necked round-bottom flask equipped with a mechanical stirrer, a gas inlet and a reflux condenser were placed phenolphthalein (25 g, 78.23 mmol) and ethylenediamine (100 mL). The reaction mixture was stirred at 120° C. for 48 h. The excess of ethylenediamine was removed by distillation. The resulting residue was slowly poured into acidified cold water and the precipitated solid was separated by filtration. The obtained solid was dissolved in hot water and the solution was treated with 10% aqueous potassium hydroxide solution while hot. The pH of solution was adjusted to 8 and the separated solid was collected by filtration. The product was purified by recrystallization from a mixture of ethanol and water (1:1, v/v). Yield: 22.6 g (80%). M.P: 260° C. IR (cm$^{-1}$): 1658 (C=O). $^1$H NMR (400 MHz, DMSO-d$_6$) δ/ppm 7.65 (d, 1H), 7.55-7.44 (m, 1H), 7.44-7.37 (m, 1H), 7.34 (d, 1H), 6.91 (d, 4H, Ar—H meta to Phenolic OH), 6.69 (d, 4H, Ar—H ortho to Phenolic OH), 3.34-3.08 (m, 6H, —NH$_2$, CH$_2$, Phenolic OH), 1.92-1.74 (m, 2H).

B) Synthesis of Phenolphthalein N-(3-maleimidoethyl)lactam

Into a 500 mL two-necked round-bottom flask equipped with a mechanical stirrer, a gas inlet and a reflux condenser were placed phenolphthalein N-(3-aminoethyl)lactam (10 g, 27.76 mmol), maleic anhydride (5.45 g, 55.53 mmol) and glacial acetic acid (100 mL). The reaction mixture was stirred at 120° C. for 12 h. The reaction mixture was cooled to 25° C. and slowly poured into an ice cold-water. The solid product was collected by filtration. The product was dissolved in ethyl acetate and the solution was washed with water (3×100 mL). The ethyl acetate solution was dried over anhydrous sodium sulphate, filtered and ethyl acetate was removed by evaporation under reduced pressure. The crude product was purified by column chromatography using pet ether:ethyl acetate (30:70, v/v) as an eluent to afford pure phenolphthalein N-(3-maleimidoethyl)lactam. (FIG. 1)
Yield: 6.8 g (56%), MP: 288° C., IR (cm$^{-1}$): 1700 (C=O). $^1$H NMR (500 MHz, DMSO-d$_6$) δ/ppm 9.58 (br. s., 2H Phenolic OH), 7.69 (d, 1H), 7.59-7.51 (m, 1H), 7.49-7.41 (m, 1H), 7.37 (d, 1H), 6.93 (d, 4H, Ar—H meta to Phenolic OH), 6.81 (s, 2H, Maleimide), 6.72 (d, 4H, Ar—H ortho to Phenolic OH), 3.56 (t, 2H), 3.01 (t, 2H).

Example: 2

Synthesis of Polyester by Low Temperature Solution Polycondensation of Phenolphthalein N-(3-maleimidoethyl)lactam and Isophthaloyl Chloride Into a 100 mL three-necked round bottom flask equipped with a magnetic stirrer, a nitrogen gas inlet and a calcium chloride guard tube were placed of phenolphthalein N-(3-maleimidoethyl)lactam (0.50 g, 1.13 mmol), dichloromethane (7 mL), and triethylamine (0.45 mL, 3.24 mmol), and the solution was cooled to 0° C. To the reaction mixture, the solution of isophthaloyl chloride (0.23 g, 1.135 mmol) in dichloromethane (10 mL) was added drop wise over a period of 20 min. The reaction mixture was stirred at 0° C. for 30 min and at 25° C. for 1 h. The viscous reaction mixture was diluted with dichloromethane (5 mL), and the solution was poured slowly into n-hexane (50 mL) to precipitate the polymer. The precipitated polymer was isolated by filtration, washed with water (5×100 mL) followed by washing with methanol (2×50 mL) and dried at 50° C. under reduced pressure for 20 h. (FIG. 2)

Advantages of the Invention

Inexpensive and easily available raw materials used
Simple and cost-effective process
Bisphenol monomers containing pendant maleimide group connected via alkylene spacer
Polymers containing pendant maleimide groups are capable of undergoing thiol-ene reaction and Diels-Alder reaction to form graft copolymers
Polymers containing pendant maleimide groups can be crosslinked thermally or by using bis-furan reagents into thermosetting resins.

We claim:

1. A compound of Formula (I)

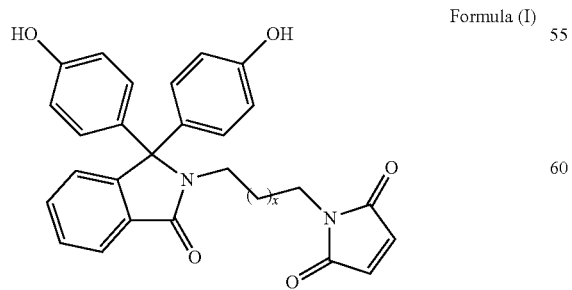

Formula (I)

wherein, x is an integer selected from 0 to 10.

2. A process for the synthesis of compound of Formula I

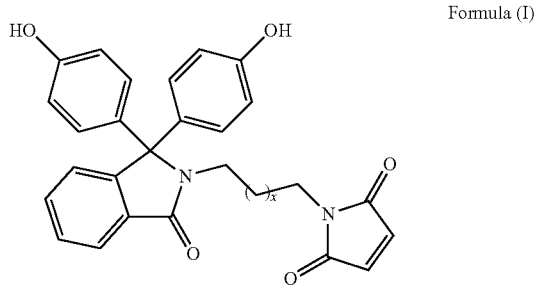

Formula (I)

wherein, x is an integer selected from 0 to 10 comprising the steps of:
a. stirring the reaction mixture comprising alkylenediamine and phenolphthalein in the molar ratio ranging between 10:1 to 20:1 for period in the range of 45 to 55 h at temperature in the range of 100 to 150° C. to afford phenolphthalein N-(aminoalkyl)lactam; and
b. stirring the reaction mixture comprising phenolphthalein N-(aminoalkyl)lactam as obtained in step (a), maleic anhydride and glacial acetic acid for period in the range of 10 to 15 h at temperature in the range of 100 to 120° C. to afford compound of Formula I.

3. The process as claimed in claim 2, wherein the compound of Formula (I) is phenolphthalein N-(maleimidoethyl)lactam.

4. A process for the synthesis of polyesters of formula II,

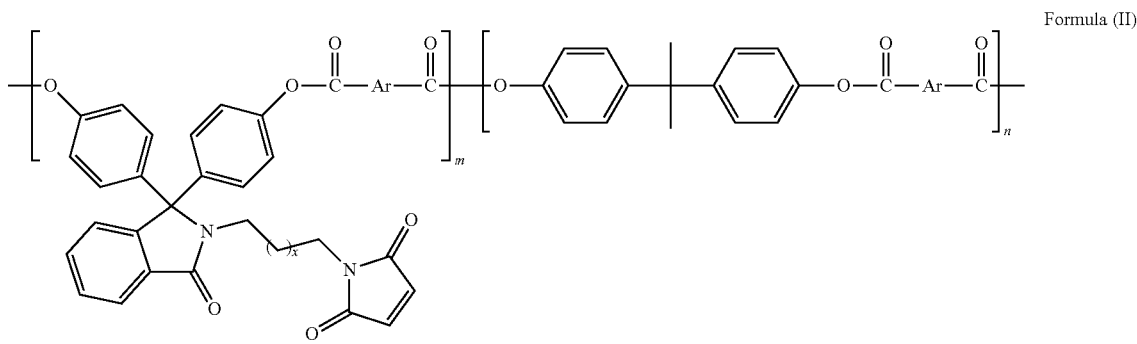

Formula (II)

wherein; x is selected from 0 to 10 and Ar is selected from

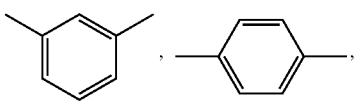

or mixture thereof, wherein the process comprising the steps of:
a) adding a solution of isophthaloyl chloride in dichloromethane to a compound of Formula I

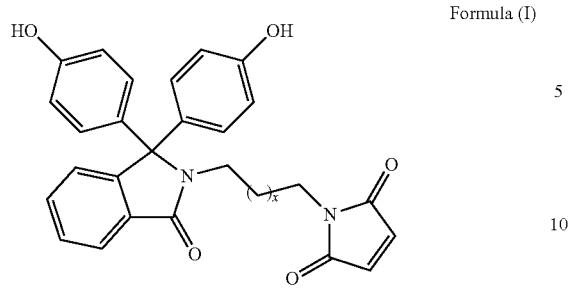

Formula (I)

wherein, x is an integer selected from 0 to 10 in dichloromethane in the presence of triethylamine and maintaining the reaction temperature at 0 to 10° C.; and b) stirring the reaction mixture of step (a) for period in the range of 20 to 30 min to get desired aromatic polyester of Formula (II).

5. A polymer comprising the recurring units of compound of formula I as defined in claim 1, wherein the polymers are selected from polycarbonates, polyether sulfones, polyetherketones, epoxy resins or polyesters.

\* \* \* \* \*